United States Patent [19]

Takase et al.

[11] Patent Number: 5,629,442
[45] Date of Patent: May 13, 1997

[54] PROCESS FOR PRODUCING α-HYDROXYIMINOPHENYLACETONITRILES

[75] Inventors: Akira Takase, Otsu; Hiroyuki Kai, Yamatokoriyama; Moriyasu Masui, Yokkaichi; Katuhisa Masumoto, Ibaraki; Akihiko Nakamura, Takatsuki; Yujiro Kiyoshima, Oita; Mikio Sasaki, Ibaraki, all of Japan

[73] Assignees: Shionogi & Co., Ltd.; Sumitomo Chemical Company, Ltd., Osaka, Japan

[21] Appl. No.: 392,860

[22] PCT Filed: Jul. 2, 1993

[86] PCT No.: PCT/JP94/01076

§ 371 Date: May 11, 1995

§ 102(e) Date: May 11, 1995

[87] PCT Pub. No.: WO95/01329

PCT Pub. Date: Jan. 12, 1995

[30] Foreign Application Priority Data

Jul. 2, 1993 [JP] Japan .................. 5-164710
Jul. 2, 1993 [JP] Japan .................. 5-164711

[51] Int. Cl.⁶ ........................................ C07C 255/01
[52] U.S. Cl. ........................................ 558/408
[58] Field of Search ................................ 558/408

[56] References Cited

U.S. PATENT DOCUMENTS 4,233,233  11/1980  Schroer et al. .

FOREIGN PATENT DOCUMENTS 0132124      7/1984   European Pat. Off. .
0468775A1    7/1991   European Pat. Off. .
596692A2    11/1993   European Pat. Off. .
54-163548   12/1979   Japan .
489464       3/1992   Japan .
6219986      8/1994   Japan .

*Primary Examiner*—Johann Richter
*Assistant Examiner*—John Peabody
*Attorney, Agent, or Firm*—Birch, Stewart, Kolasch & Birch, LLP

[57] ABSTRACT

A process is disclosed to produce an α-hydroxyiminophenylacetonitrile of the general formula [II]:

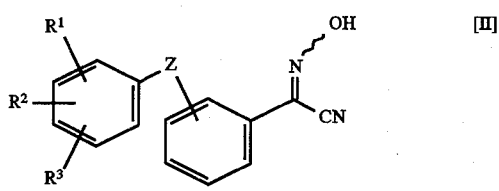

wherein $R^1$, $R^2$, $R^3$ and Z are each as defined in the specification, characterized in that a crude nitrile containing a phenylacetonitrile of the general formula [I]:

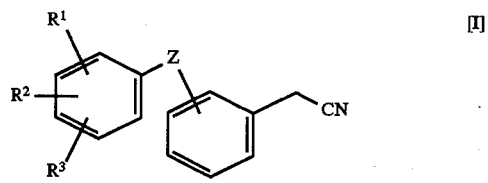

wherein $R^1$, $R^2$, $R^3$ and Z are each as defined in the specification, is reacted with an alkyl nitrite in the presence of a base, after which the reaction mixture is extracted with water and then the separated aqueous layer is neutralized with an acid. According to this production process, the desired α-hydroxyiminophenylacetonitrile can be produced with high purity, in high yield and with ease by extracting the reaction mass with water and then neutralizing the separated aqueous layer with an acid.

9 Claims, No Drawings

PROCESS FOR PRODUCING α-HYDROXYIMINOPHENYLACETONITRILES

This applications is 371 of PCT/JP94/01076 filed Jul. 1, 1994.

TECHNICAL FIELD

The present invention relates to a process for producing α-hydroxyimino- phenylacetonitriles.

BACKGROUND ART

α-Hydroxyiminophenylacetonitriles are known as intermediates of plant growth promoting agents, agricultural fungicides, or the like (e.g., Japanese Patent Publication No. 62-54096).

As the process of their production, for example, it is also known that α-hydroxyiminophenylacetonitriles are produced by reacting phenylacetonitriles with alkyl nitrites in an alcohol solvent in the presence of an aqueous base solution, then neutralizing with an acid, removing low-boiling contents by distillation, and collecting the precipitated solids by filtration (e.g., Japanese Patent Laid-open Publication No. 54-163548).

In the case where crude starting materials containing impurities are used as the starting material phenylacetonitriles, however, there is a difficult point that α-hydroxyiminophenylacetonitriles as the desired products have a decreased purity, if produced by the above process.

In the case where crude materials are used after being purified by distillation or other techniques, there is also a difficult point that complicated steps for separation and purification are required and the yield is decreased by their operations or the like.

DISCLOSURE OF THE INVENTION

The present inventors have extensively studied to develop a more favorable process for producing α-hydroxyiminophenylacetonitriles by use of crude phenylacetonitriles. As a result, they have found that the desired α-hydroxyiminophenylacetonitriles can be produced with high purity, in high yield and with ease by reacting the crude phenylacetonitriles with alkyl nitrites, extracting the reaction mass with water, and then neutralizing the separated aqueous layer with an acid, and they have further made various studies, thereby completing the present invention.

Thus, the present invention provides an industrially favorable process for producing an α-hydroxyiminophenylacetonitrile of the general formula [II]:

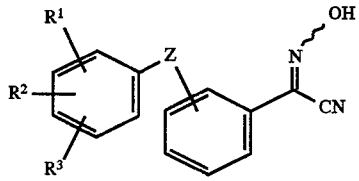

wherein $R^1$, $R^2$, $R^3$ and Z are each as defined below, characterized in that a crude nitrile containing a phenylacetonitrile of the general formula [I]:

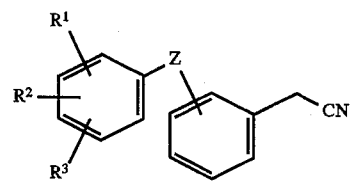

wherein $R^1$, $R^2$ and $R^3$ are the same or different and are independently hydrogen, halogen, nitro, trifluoromethyl, $C_1$-$C_5$ alkyl or $C_1$-$C_5$ alkoxy, and Z is —O—, —OCH$_2$—, —S— or —SCH$_2$—, is reacted with an alkyl nitrite; extracting the reaction mixture with water; and then neutralizing the separated aqueous layer with an acid.

The present invention will hereinafter be explained in detail.

As the substituents $R^1$, $R^2$ and $R^3$ of the phenylacetonitrile [I] as the starting material component of the present invention, there can be mentioned, for example, hydrogen; halogen such as fluorine, chlorine, bromine and iodine; nitro; trifluoromethyl; $C_1$-$C_5$ alkyl such as methyl, ethyl, propyl, isopropyl, butyl, isobutyl, tert-butyl and pentyl; and $C_1$-$C_5$ alkoxy such as methoxy, ethoxy, propoxy, isopropoxy, butoxy, isobutoxy, tert-butoxy, pentyloxy, and the like.

As the Z, there can be mentioned oxygen, oxymethylene, sulfur, thiomethylene, and the like.

As the specific compound of the phenylacetonitrile [I], there can be mentioned, for example, 2-phenoxyphenylacetonitrile, 3-phenoxyphenylacetonitrile, 4-phenoxyphenylacetonitrile, 2-(2-fluorophenoxy) phenylacetonitrile, 4-(3-chlorophenoxy)phenylacetonitrile, 3-(4-bromophenoxy)phenylacetonitrile, 3-(3-nitrophenoxy) phenylacetonitrile, 2-(4-nitrophenoxy)phenylacetonitrile, 2-(2-methoxyphenoxy)phenylacetonitrile, 4-(3-methoxyphenoxy)phenylacetonitrile, 3-(2-ethoxyphenoxy) phenylacetonitrile, 4-(2-isopropoxyphenoxy) phenylacetonitrile, 4-(4-butoxyphenoxy)phenylacetonitrile, 3-(2-methoxy-5-nitrophenoxy)phenylacetonitrile, 2-(2,3-dimethoxyphenoxy)phenylacetonitrile, 2-(3,4,5-trimethoxyphenoxy)phenylacetonitrile, 2-(phenylthio) phenylacetonitrile, 4-(4-nitrophenylthio)phenylacetonitrile, 3-(2-methoxyphenylthio)phenylacetonitrile, 2-(phenoxymethyl)phenylacetonitrile, 3-(phenoxymethyl) phenylacetonitrile, 4-(phenoxymethyl)phenylacetonitrile, 2-(2-fluorophenoxymethyl)phenylacetonitrile, 4-(3-fluorophenoxymethyl)phenylacetonitrile, 2-(3-chlorophenoxymethyl)phenylacetonitrile, 2-(4-chlorophenoxymethyl)phenylacetonitrile, 3-(4-bromophenoxymethyl)phenylacetonitrile, 4-(3-nitrophenoxymethyl)phenylacetonitrile, 2-(3-trifluoromethylphenoxymethyl)phenylacetonitrile, 2-(2-methylphenoxymethyl)phenylacetonitrile, 2-(4.-ethylphenoxymethyl)phenylacetonitrile, 3-(2-propylphenoxymethyl)phenylacetonitrile, 2-(4-isopropylphenoxymethyl)phenylacetonitrile, 3-(3-t-butylphenoxymethyl)phenylacetonitrile, 2-(2-methoxyphenoxymethyl)phenylacetonitrile, 2-(4-butoxyphenoxymethyl)phenylacetonitrile, 2-(2,4-dichlorophenoxymethyl)phenylacetonitrile, 2-(2,4-difluorophenoxymethyl)phenylacetonitrile, 3-(3-chloro-4-fluorophenoxymethyl)phenylacetonitrile, 4-(4-chloro-2-nitrophenoxymethyl)phenylacetonitrile, 2-(4-chloro-2-methylphenoxymethyl)phenylacetonitrile, 3-(2-fluoro-6-methoxyphenoxymethyl)phenylacetonitrile, 2-(3-methyl-4-nitrophenoxymethyl)phenylacetonitrile, 3-(2-methoxy-4-nitrophenoxymethyl)phenylacetonitrile, 2-(2,4-dimethylphenoxymethyl)phenylacetonitrile, 2-(2,5- dimethylphenoxymethyl)phenylacetonitrile, 4-(2-methoxy-4-methylphenoxymethyl)phenylacetonitrile, 2-(3,4-dimethoxyphenoxymethyl)phenylacetonitrile, 3-(2,4,5-trichlorophenoxymethyl)phenylacetonitrile, 4-(2,3-difluoro-6-nitrophenoxymethyl)phenylacetonitrile, 3-(4-chloro-3,5-dimethylphenoxymethyl)phenylacetonitrile, 2-(2,3,5-trimethylphenoxymethyl)phenylacetonitrile, 2-(3,4,5-trimethoxyphenoxymethyl)phenylacetonitrile, 2-(phenylthiomethyl)phenylacetonitrile, 2-(4-fluorophenylthiomethyl)phenylacetonitrile, 3-(4-nitrophenylthiomethyl)phenylacetonitrile, 4-(2-methoxyphenylthiomethyl)phenylacetonitrile, 3-(3,4-dichlorophenylthiomethyl)phenylacetonitrile, 2-(2,4-dimethylphenylthiomethyl)phenylacetonitrile, 2-(2,5-dimethylphenylthiomethyl)phenylacetonitrile, and the like.

The crude nitrile as the starting material of the present invention may contain, in addition to the phenylacetonitrile [I] as described above, for example, the starting materials and by-products in the production of the phenylacetonitrile [I] as the impurities.

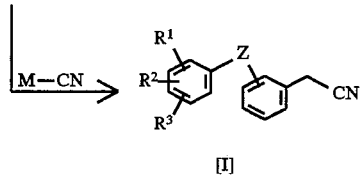

Also, in the case where the phenylacetonitrile [I] is produced through the following route (2), there can be mentioned as the impurities, α-substituted, α'-haloxylene derivative [IV'], α,α-disubstituted xylene derivative [VIII], and the like, as well as α,α-dihaloxylene derivative [VI], and the starting materials and by-products in its production.

(Route 2)

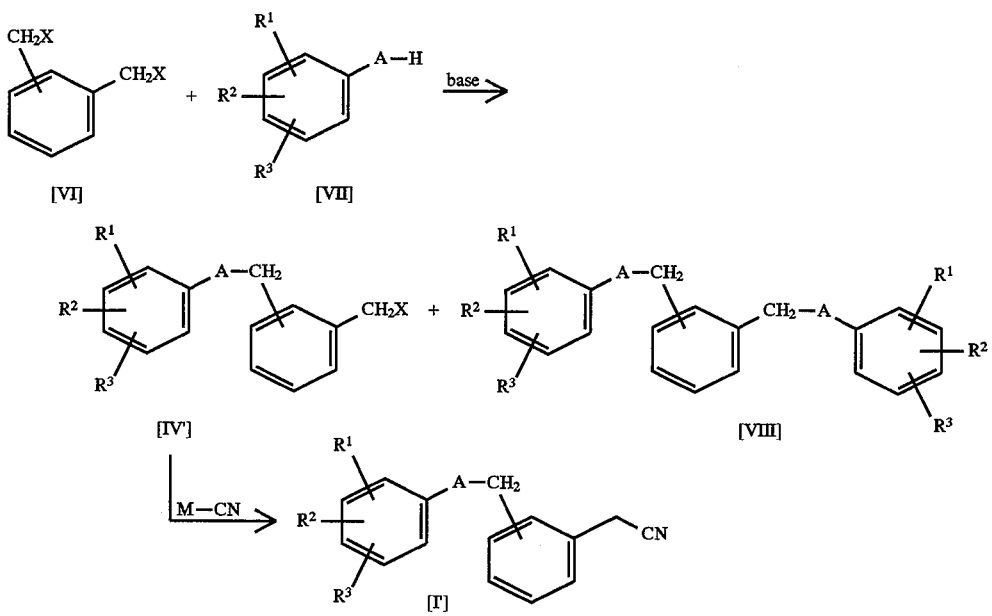

As such impurities, for example, in the case where the phenylacetonitrile [I] is produced through the following route (1), there can be mentioned, for example, toluene derivative [III], benzyl halide derivative [IV], benzal halide derivative [V], and the like.

(Route 1)

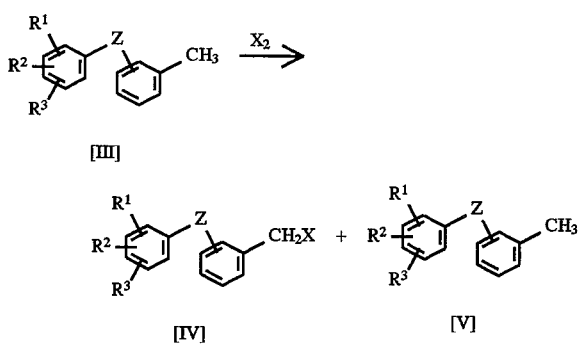

In the reaction of the crude nitrile with the alkyl nitrite, there can be mentioned as the alkyl nitrite to be used, for example, methyl nitrite, ethyl nitrite, n-propyl nitrite, iso-propyl nitrite, n-butyl nitrite, amyl nitrite, hexyl nitrite, and the like. Such an alkyl nitrite may be used after being synthesized by the known methods or may be obtained from commercial sources.

The amount of the alkyl nitrite to be used is 0.8 to 10 times, preferably 1 to 2 times, the moles of the phenylacetonitrile [I].

As the base, there can be usually used, for example, inorganic bases such as hydroxides of alkali metals, e.g., sodium hydroxide and potassium hydroxide; and carbonates of alkali metals, e.g., sodium carbonate and potassium carbonate; and organic bases can also be used, such as alkoxides of alkali metals, e.g., sodium ethoxide. Two or more kinds of these bases can be used in combination.

The amount of the base to be used is usually 0.8 to 10 times, preferably 1 to 2 times, the moles of the phenylacetonitrile [I].

Also, the reaction is usually effected in the presence of a solvent. As such a solvent, there can be mentioned solvents substantially inert to the reaction, for example, alcohols such as methanol and ethanol; ketones such as acetone, methyl ethyl ketone and methyl isobutyl ketone; aliphatic hydrocarbons such as hexane and heptane; aromatic hydrocarbons such as benzene, toluene and xylene; and halogenated hydrocarbons such as dichloromethane, 1,2-dichloroethane, chlorobenzene and α-dichlorobenzene. Two or more kinds of these solvents can be used in combination. Also, hydrous alcohols can be used.

The amount of the solvent to be used is usually about 1 to 10 times the weight of the crude phenylacetonitrile.

The reaction is effected in the presence of a base, usually at a temperature of from 0° C. to the refluxing temperature of the reaction mixture, preferably from 0° to 40° C.

Thus, the reaction mixture containing the α-hydroxyiminophenylacetonitrile [II] as the desired product is obtained, and this mixture can be extracted with water to separate the desired product [II] in the aqueous layer from the impurities in the organic layer.

In the water extraction, water is added to the reaction mixture. When a hydrophilic organic solvent is contained in the reaction mixture, the reaction mixture is usually used after the removal of the hydrophilic organic solvent by a technique such as concentration.

Water is added so that the total amount thereof becomes usually about 1 to 20 times the weight of the crude phenylacetonitrile used.

Further, the addition of a water-insoluble or sparingly water-soluble organic solvent is also preferable; for example, aliphatic hydrocarbons such as hexane and heptane; aromatic hydrocarbons such as benzene, toluene and xylene; ethers such as diethyl ether; ketones such as methyl isobutyl ketone; halogenated hydrocarbons such as dichloromethane, 1,2-dichloroethane, chlorobenzene and o-dichlorobenzene, and the like. The addition of such an organic solvent makes it possible to separate the impurities with high efficiency.

In that case, the organic solvent is added so that the total amount thereof becomes usually about 0.1 to 5 times the weight of water added.

Further, the aqueous layer separated by the extraction procedure can be washed with a water-insoluble or sparingly water-soluble organic solvent.

Then, the separated aqueous layer is neutralized with an acid, but it can also be supplied as the starting material in the subsequent step without conducting neutralization. As the acid when the acid is used, either an organic acid or an inorganic acid may be used, and preferred is an inorganic acid. As the preferred inorganic acid, there can be mentioned, for example, mineral acids such as hydrochloric acid, sulfuric acid and nitric acid.

The acid is used until the pH of the system becomes 7 or lower, preferably 4 or lower, and more preferably 2 or lower.

The neutralization with an acid is usually effected at −10° to 100° C., preferably 0° to 40° C.

Thus, the desired product α-hydroxyiminophenylacetonitrile [II] is obtained, and the desired product can be isolated by the ordinary methods. For example, the separation can be achieved by filtration when the desired product is obtained as crystals, or for example, by extraction with an organic solvent, followed by removal of the organic solvent by distillation, when obtained in an oily product.

Next, the following will describe the process for producing a crude nitrile as the starting material of the present invention.

The crude nitrile of the present invention, although it is not particularly limited, can be produced, for example, by the above-described route (1), (2) or the like.

In the case where the crude nitrile is produced through the route (1), the crude nitrile containing the phenylacetonitrile [I] can be produced, for example, by reacting the toluene derivative [III] with halogen to produce the benzyl halide derivative [IV] and then reacting this derivative with a cyano compound.

As the substituents $R^1$, $R^2$ and $R^3$ in the toluene derivative [III], there can be mentioned, for example, hydrogen, halogen, nitro, $C_1$–$C_5$ alkoxy, and the like, in the same manner as described above. As the Z, there can be mentioned —O—, —$OCH_2$—, —S— or —$SCH_2$—, and the like.

As the specific compound, there can be mentioned, for example, 1-methyl-2-phenoxybenzene, 1-(2-fluorophenoxy)-2-methylbenzene, 1-(4-bromophenoxy)-3-methylbenzene, 1-(2-methoxyphenoxy)-2-methylbenzene, 1-(2-isopropoxyphenoxy)-4-methylbenzene, 1-(4-butoxyphenoxy)-4-methylbenzene, 1-(2,3-dimethoxyphenoxy)-2-methylbenzene, 1-methyl-2-(3,4,5-trimethoxyphenoxy)benzene, 1-methyl-2-(phenylthio)benzene, 1-(2-methoxyphenylthio)-3-methylbenzene, and the like.

The benzyl halide derivative [IV] can also be produced from the toluene derivative [III], for example, in accordance with the methods as described in Japanese Patent Laid-open Publication Nos. 56-166142 and 57-18644.

In the reaction of the benzyl halide derivative [IV] with the cyano compound, the benzyl halide derivative [IV] to be used may be a crude benzyl halide derivative containing impurities such as the toluene derivative [III] and the benzal halide derivative [V], or of course, it may have high purity.

As the cyano compound, there can be mentioned, for example, sodium cyanide, potassium cyanide, or mixtures thereof. It can also be used after prepared by reacting hydrogen cyanide with an alkali metal salt such as sodium hydroxide, potassium hydroxide, sodium carbonate and potassium carbonate in the reaction system. The amount of such a cyano compound to be used is usually 0.8 to 10 times, preferably 1 to 2 times, the moles of the benzyl halide derivative [IV].

The reaction is usually effected in the presence of a solvent. As such a solvent, there can be mentioned, for example, aprotic polar solvents such as dimethylformamide and dimethylsulfoxide. In the presence of a phase transfer catalyst, water and a water-insoluble or sparingly water-soluble organic solvent can also be used. As such an organic solvent, there can be mentioned, for example, aliphatic hydrocarbons such as hexane and heptane; aromatic hydrocarbons such as benzene, toluene and xylene; halogenated hydrocarbons such as dichloromethane, 1,2-dichloroethane, chlorobenzene and o-dichlorobenzene; and mixtures thereof. The solvent is used at an amount which is usually 1 to 10 times the weight of the benzyl halide derivative used.

As the phase transfer catalyst, there can be mentioned quaternary ammonium salts, quaternary phosphonium salts, and the like. Preferred are quaternary ammonium salts. As the quaternary ammonium salt, there can be usually used, for example, tetra-n-butylammonium bromide, benzyltriethylammonium chloride, or the like.

The amount of the phase transfer catalyst to be used is usually 0.001 to 1 time, preferably 0.005 to 0.1 times, the moles of the benzyl halide derivative [IV].

The reaction is usually effected at a temperature of from 0° C. to the refluxing temperature of the solvent.

Thus, the cyano compound is selectively reacted with the benzyl halide derivative [IV] to form the phenylacetonitrile derivative [I], while the toluene derivative [III] and the benzal halide derivative [V] are kept in substantially quantitative manner.

The reaction mixture obtained can be subjected to the reaction of the present invention as the crude nitrile after treated by the ordinary methods, for example, after washed with water, followed by removal of the solvent by distillation, or further after the toluene derivative [III] and the like are removed by distillation.

Also, in the case where the crude nitrile is produced through the route (2), the crude nitrile containing the phenylacetonitrile [I'] can be produced, for example, by reacting the $\alpha,\alpha'$-dihaloxylene derivative [VI] with the phenol derivative [VII] in the presence of a base to produce the $\alpha$-substituted, $\alpha'$-haloxylene derivative [IV'] and then reacting this derivative with a cyano compound.

As the specific compound of the $\alpha,\alpha'$-dihaloxylene derivative [VI], there can be mentioned, for example, $\alpha,\alpha'$-dichloro-o-xylene, $\alpha,\alpha'$-dichloro-m-xylene, $\alpha,\alpha'$-dichloro-p-xylene, $\alpha,\alpha'$-dibromo-o-xylene, $\alpha,\alpha'$-dibromo-m-xylene, $\alpha,\alpha'$-dibromo-p-xylene, and the like.

As the substituents $R^1$, $R^2$ and $R^3$ in the phenol derivative [VII], there can be mentioned, for example, hydrogen, halogen, nitro, $C_1$–$C_5$ alkyl, $C_1$–$C_5$ alkoxy, and the like, in the same manner as described above. As the A, there can be mentioned —O—, —S—, and the like. As the specific compound, there can be mentioned, for example, phenol, 2-fluorophenol, 3-chlorophenol, 4-chlorophenol, 4-bromophenol, 3-trifluoromethylphenol, 2-methylphenol, 4-i-propylphenol, 3-t-butylphenol, 2-methoxyphenol, 4-butoxyphenol, 2,4-dichlorophenol, 2,5-dichlorophenol, 3-chloro-4-fluorophenol, 4-fluoro-3-methylphenol, 4-chloro-2-methylphenol, 2-fluoro-6-methoxyphenol, 2,4-dimethylphenol, 2,5-dimethylphenol, 2-methoxy-4-methylphenol, 3,4-dimethoxyphenol, 2,4,5-trichlorophenol, 4-chloro-3,5-dimethylphenol, 2,3,5-trimethylphenol, 3,4,5-trimethylphenol, thiophenol, 4-fluorothiophenol, 2-chlorothiophenol, 3-bromothiophenol, 2-methoxythiophenol, 2,5-dichlorothiophenol, 3,4-dichlorothiophenol, 2,4-dimethylthiophenol, 2,5-dimethylthiophenol, 3,5-dimethylthiophenol, and the like.

The $\alpha,\alpha'$-dihaloxylene derivative [VI] is used at an amount which is usually not less than 1.5 times, preferably 2 to 6 times, the moles of the phenol derivative [VII].

As the base, there can be mentioned, for example, hydroxides or carbonates of alkali metals or alkaline earth metals, such as sodium hydroxide, potassium hydroxide, magnesium hydroxide, calcium hydroxide, barium hydroxide, sodium carbonate and potassium carbonate. The amount to be used is usually 0.7 to 1.5 times, preferably 0.9 to 1.2 moles, the moles of the phenol derivative [VII].

The reaction is usually effected by adding dropwise a base to a mixture of the solvent, $\alpha,\alpha'$-dihaloxylene derivative [VI], phenol derivative [VII], and the like.

As the solvent, there can be usually used water or a mixed solvent of water and an organic solvent. As such an organic solvent, there can be mentioned, for example, aromatic hydrocarbons such as toluene and xylene; aliphatic hydrocarbons such as hexane, cyclohexane and heptane; halogenated hydrocarbons such as chlorobenzene, dichlorobenzene, chloroform and 1,2-dichloroethane; ketone such as acetone and methyl isobutyl ketone; ethers such as diisopropyl ether and methyl-t-butyl ether, and the like.

The amount of the solvent to be used is usually about 1 to 20 times the weight of the phenol derivative [VII].

Also, when the reaction is effected in the presence of a two-layer solvent system consisting of an organic solvent and water, it is also effective to allow a phase transfer catalyst to coexist therewith. As the phase transfer catalyst, there can be mentioned, for example, quaternary ammonium salts such as tetra-n-butylammonium bromide and benzyltriethylammonium chloride. The amount to be used is usually 0.02 to 0.1 times the moles of the phenol derivative [VII].

The reaction is usually effected at about 20° to 100° C. The benzyl halide derivative [IV'] formed can be isolated by a technique such as extraction, distillation or recrystallization.

Then, the crude nitrile containing the phenylacetonitrile [I'] can be produced by reacting the benzyl halide derivative [IV'] with the cyano compound, and the benzyl halide derivative [IV'] to be used may be a crude benzyl halide derivative containing impurities such as $\alpha,\alpha'$-disubstituted xylene derivative [VIII] and the starting materials and by-products in the production of $\alpha,\alpha'$-dihaloxylene derivative [VI], or of course, it may have high purity.

The crude nitrile containing the phenylacetonitrile [I'] can be produced by conducting the cyanation and post-treatment, for example, in the same manner as in the above route (1), and subjected to the reaction of the present invention.

EXAMPLES

The present invention will be further illustrated by the following Examples, but the present invention is not limited only to these Examples.

Reference Example 1

Production of starting materials (1) Production of 2-phenoxybenzyl bromide

First, 120.0 g (651 mmol) of 2-phenoxytoluene was dissolved in 240 g of chlorobenzene, and the solution was heated to 135°–140° C. for reflux. To this solution was introduced 105.0 g (657 mmol) of bromine gas heated to 140°–150° C. over 4 hours, and the stirring was further continued at 135°–140° C. for 1.5 hours.

Then, the reaction mixture was allowed to stand for cooling to room temperature, which afforded a chlorobenzene solution (408.1 g) containing 122.9 g (467 mmol, 71.7% yield)of 2-phenoxybenzyl bromide, 16.5 g (89.3 mmol, 13.7% recovery) of 2-phenoxytoluene and 32.0 g (93.6 mmol, 14.4% yield) of 2-phenoxybenzal bromide.

(2) Production of 2-phenoxyphenylacetonitrile

To the above chlorobenzene solution (393.3 g) was added 7.25 g (22.5 mmol) of tetra-n-butylammonium bromide, and the mixture was heated to 78°–82° C., to which 80.9 g (495 mmol) of 30% aqueous sodium cyanide solution was added dropwise over 3 hours, and the stirring was further continued at 78°–82° C. for 2 hours.

Then, the mixture was allowed to stand for cooling to room temperature, and the reaction mixture separated into two layers was subjected to phase separation to give the organic layer. The organic layer was washed with water and then concentrated. Thus, a mixture containing 92.6 g (442 mmol, 98.3% yield) of 2-phenoxyphenylacetonitrile, 15.8 g (85.7 mmol, 99.7% recovery)of 2-phenoxytoluene and 30.9 g (90.4 mmol, 100% recovery) of 2-phenoxybenzal bromide was obtained.

Example 1

Production example of α-hydroxyimino-2-phenoxyphenylacetonitrile

(1) Preparation of methyl nitrite

A mixture comprising 35.6 g (516 mmol) of sodium nitrite, 17.9 g (559 mmol) of methanol and 21.5 g of water was gently stirred at room temperature to give a suspension. To this suspension was added dropwise 44.28 g (271 mmol) of 60% sulfuric acid with stirring at room temperature over 8 hours, which gave methyl nitrite (about 516 mmol) in gas form over 8 hours for use in the subsequent reaction.

(2) Production of α-hydroxyimino-2-phenoxyphenylacetonitrile

First, 21.3 g (516 mmol) of sodium hydroxide was dissolved in 116.3 g of methanol, and the solution was mixed with a chlorobenzene solution (367.1 g) of a mixture containing 90.0 g (430 mmol) of 2-phenoxyphenylacetonitrile, 15.3 g (83.3 mmol) of 2-phenoxytoluene and 30.1 g (87.9 mmol) of 2-phenoxybenzal bromide, which had been produced in Reference Example 1, followed by stirring at room temperature.

To this mixture was introduced 31.5 g (about 516 mmol) of methyl nitrite prepared in paragraph (1) over 8 hours, and the stirring was further continued at room temperature for 15 hours. The reaction mixture was concentrated to remove methanol and other low-boiling contents, after which 300 ml of water and 300 ml of toluene were added thereto, followed by extraction and phase separation. The aqueous layer obtained was further washed twice with 150 ml of toluene.

The organic layers obtained were combined together and then concentrated, which afforded a mixture containing 0.64 g (3 mmol, 0.7% recovery) of 2-phenoxyphenylacetonitrile, 15.3 g (83.3 mmol, 100% recovery) of 2-phenoxytoluene and 22.4 g (65.6 mmol, 74.6% recovery) of 2-phenoxybenzal bromide.

On the other hand, the aqueous layer obtained was cooled at 0°–5° C., and the pH of the reaction mixture was adjusted to 2 or lower by adding dropwise 30.3 g (309 mmol) of 97% sulfuric acid.

Then, 400 ml of toluene was added at room temperature, followed by extraction and phase separation, and the aqueous layer was further extracted once with 150 ml of toluene. The organic layers obtained were combined together, and washed with 150 ml of saline solution, followed by concentration, which afforded 93.7 g (393 retool, 91.4% yield) of α-hydroxyimino-2-phenoxyphenylacetonitrile. The purity of this product was analyzed by high performance liquid chromatography, and found to be 99.5%.

Comparative Example 1

(1) Distillation of 2-phenoxybenzyl bromide

A chlorobenzene solution (91.68 g) containing 28.97 g (110 mmol) of 2-phenoxybenzyl bromide, 4.68 g (25.4 retool) of 2-phenoxytoluene and 5.41 g (15.8 mmol)of 2-phenoxybenzal bromide, which had been produced in accordance with Reference Example 1-(1), was distilled under reduced pressure, and the fractions were collected at a boiling point of 133°–134° C./0.3 mmHg to give 16.86 g (64.1 mmol, 58.2% distillation yield) of 2-phenoxybenzyl bromide.

The analysis by gas chromatography revealed that the content was 93.8%.

(2) Distillation of 2-phenoxyphenylacetonitrile

In this section, 440.8 g of a toluene solution containing 130.9 g (626 mmol) of 2-phenoxyphenylacetonitrile, 23.8 g (129 mmol) of 2-phenoxytoluene and 41 g (120 mmol) of 2-phenoxybenzal bromide, which had been produced in accordance with Reference Example 1-(2), was distilled under reduced pressure, and the fractions were collected at a boiling point of 159° C./3 mmHg to give 101.9 g (487 mmol, 77.8% distillation yield) of 2-phenoxyphenylacetonitrile.

The analysis by gas chromatography revealed that the content was 98.2%.

Reference Example 2-(1)

Production of starting material

To 2017 g of toluene were added 840 g (4.8 tool) of α,α'-dichloro-o-xylene, 195 g (1.6 tool) of 2,5-dimethylphenol and 25.8 g (0.08 tool) of tetra-n-butylammonium bromide with stirring, to which 268 g of water was added, and the mixture was heated to 60° C.

To this mixture was added dropwise 261 g (1.76 m.31) of 27% aqueous sodium hydroxide solution over 5 hours, and the mixture was kept at the same temperature for 3 hours and then cooled to room temperature. The aqueous layer was removed by phase separation, whereas the organic layer was washed with 1000 g of 5% hydrochloric acid and washed twice with 1000 g of water, and the α,α'-dichloro-o-xylene was removed by distillation, which afforded 372 g of a mixture containing 292 g (1.12 mol, 69.9% yield) of 2-(2,5-dimethylphenoxymethyl)benzyl chloride and 64.3 g (0.186 mol, 23.2% yield) of 1,2-bis(2,5-dimethylphenoxymethyl)benzene.

A mixture comprising 241 g of water, 670 g of toluene, 60.2 g (1.23 mol) of sodium cyanide and 16.4 g (0.051 mol) of tetra-n-butylammonium bromide was heated to 80° C. with stirring, to which a mixture of 84.5 g of toluene and 338 g of the mixture produced in the foregoing was added dropwise over 5 hours, and the mixture was further kept at the same temperature for 2.75 hours.

Then, the mixture was cooled to room temperature, and the aqueous layer was removed by phase separation, whereas the organic layer was washed with 345 g of 1% aqueous sodium hydroxide solution and washed twice with 345 g of water, followed by concentration, which afforded 306 g of a mixture containing 248 g (0.987 mol, 97.1% yield) of 2-(2,5-dimethylphenoxymethyl)phenylacetonitrile and 57.5 g (0.166 mol, 98.3% recovery) of 1,2-bis(2,5-dimethylphenoxymethyl)benzene.

Reference Example 2-(2)

To 1619 g of toluene were added 788 g (4.50 mol) of α,α'-dichloro-o-xylene, 183 g (1.50 mol) of 2,5-dimethylphenol and 24.2 g (0.075 tool) of tetra-n-butyl-ammonium bromide with stirring, to which 1246 g of water was added, and the mixture was heated to 60° C.

To this mixture was added dropwise 244 g (1.65 tool) of 27% aqueous sodium hydroxide solution over 5 hours, and the mixture was kept at the same temperature for 3 hours and then cooled to room temperature. The aqueous layer was removed by phase separation, whereas the organic layer was washed with 810 g of 5% hydrochloric acid and washed twice with 810 g of water, and the α,α'-dichloro-o-xylene was removed by distillation, which afforded 364 g of a mixture containing 279 g (1.07 mol, 71.3% yield) of 2-(2, 5-dimethylphenoxymethyl)benzyl chloride and 57.7 g (0.167 mol, 22.2% yield) of 1,2-bis(2,5-dimethylphenoxymethyl)benzene. The mixture thus obtained can be used in the subsequent step after diluted by addition of toluene.

Reference Example 2-(3)

To 140.0 g of toluene were added 113.8 g (0.65 tool) of α,α'-dichloro-o-xylene, 15.9 g (0.13 mol) of 2,5-dimethylphenol and 2.10 g (0.0,365 mol) of tetra-n-butylammonium bromide with stirring, to which 108.0 g of water was added, and the mixture was heated to 60° C.

To this mixture was added dropwise 21.2 g (0.143 mol) of 27% aqueous sodium hydroxide solution over 5 hours, and the mixture was kept at the same temperature for 2 hours and then cooled to room temperature. The aqueous layer was removed by phase separation, whereas the organic layer was washed with 70.2 g of 5% hydrochloric acid and washed twice with 70.2 g of water, and the α,α'-dichloro-o-xylene was removed by distillation, which afforded 33.5 g of a mixture containing 26.4 g (0.101 mol, 77.8% yield) of 2-(2,5-dimethylphenoxymethyl)benzyl chloride and 3.08 g (0.0089 mol, 13.7% yield) of 1,2-bis(2,5-dimethylphenoxymethyl)benzene. The mixture thus obtained can be used in the subsequent step after diluted by addition of toluene.

Reference Example 2-(4)

The reaction and post-treatment were conducted in the same manner as in Reference Example 2-(3), except that 45.5 g (0.26 tool) of α,α'-dichloro-o-xylene was used, which afforded 36.7 g of a mixture containing 20.7 g (0.079 tool, 61.1% yield) of 2-(2,5-dimethylphenoxymethyl)benzyl chloride and 6.97 g (0.020 tool, 30.9% yield) of 1,2-bis(2, 5-dimethylphenoxymethyl)benzene.

Reference Example 2-(5)

To 22.8 g (0.13 mol) of α,α'-dichloro-o-xylene, 15.9 g (0.13 mol) of 2,5-dimethylphenol and 2.10 g (0.0065 mol) of tetra-n-butylammonium bromide were added 140.3 g of toluene and then 108.0 g of water, followed by stirring. To this mixture was added dropwise 21.2 g (0.143 mol)of 27% aqueous sodium hydroxide solution at 60° C. over 5 hours, and the mixture was further kept at 60° C. for 9 hours. The reaction mixture was cooled to room temperature, and the aqueous layer was removed by phase separation. The organic layer was washed with 70.2 g of 5% hydrochloric acid and then washed twice with 70.2 g of water. The organic layer was concentrated to give 25.7 g of a mixture containing 12.1 g (0.046 tool, 35.7% yield) of 2-(2,5-dimethylphenoxymethyl)benzyl chloride and 11.7 g (0.0338 mol, 52.0% yield) of 1,2-bis(2,5-dimethylphenoxymethyl) benzene.

Reference Example 3-(1)

Production of starting material

A mixture comprising 266 g of water, 66.6 g (1.36 mol) of sodium cyanide, 16.4 g (0.051 mol) of tetra-n-butylammonium bromide and 439 g of toluene was heated to 80° C. with stirring, to which 715 g of a toluene solution of a mixlitre containing 266 g (1.02 mol) of 2-(2,5-dimethylphenoxymethyl)benzyl chloride and 56.5 g (0.163 mol) of 1,2-bis(2,5-dimethylphenoxymethyl)benzene was added dropwise, and the mixture was further kept at the same temperature for 3 hours.

Then, the mixture was cooled to room temperature, and the aqueous layer was removed by phase separation, whereas the organic layer was washed three times with 379 g of 1% aqueous sodium hydroxide solution, washed with 379 g of water and then 379 g of 10% saline solution, which afforded 1141 g of the organic layer. To 716 g of this organic layer was added 43.3 g (0.064 mol) of 11% aqueous sodium hypochlorite solution, and the mixture was stirred at 23° C for 3 hours, after which the precipitated insoluble matters were removed by filtration. The organic layer was washed with 100 g of 10% sodium sulfite, then with 100 g of water and further with 10% saline solution, and concentrated, which afforded 531.4 g of a mixture containing 157.1 g (0.625 mol, 97.7% yield) of 2-(2,5-dimethylphenoxymethyl) phenylacetonitrile and 35.4 g (0.102 mol, 99.5% recovery) of 1,2-bis(2,5-dimethylphenoxymethyl)benzene.

Reference Example 3-(2)

In this section, 372 g of a mixture containing 292 g (1.12 tool, 69.9% yield) of 2-(2,5-dimethylphenoxymethyl)benzyl chloride and 64.3 g (0.186 mol, 23.2% yield) of 1,2-bis(2, 5-dimethylphenoxymethyl)benzene was obtained in accordance with Reference Example 2-(2).

A mixture comprising 241 g of water, 60.2 g (1.23 tool) of sodium cyanide, 16.4 g (0.051 mol) of tetra-n-butylammonium bromide and 670 g of toluene was heated to 80° C. with stirring, to which a mixture obtained by adding 84.5 g of toluene to 338 g of the mixture produced in the foregoing was added dropwise over 5 hours, and the mixture was further kept at the same temperature for 2.75 hours.

Then, the mixture was cooled to room temperature, and the aqueous layer was removed by phase separation, whereas the organic layer was washed with 345 g of 1% aqueous sodium hydroxide solution and washed twice with 345 g of water, and concentrated, which afforded 306 g of a mixture containing 248 g (0.987 tool, 97.1% yield) of 2-(2,5-dimethylphenoxymethyl)phenylacetonitrile and 57.5 g (0.166 mol, 8.3% recovery) of 1,2-bis(2,5-dimethylphenoxymethyl)benzene.

Example 2

To 50.42 g of toluene were added 29.77 g of the mixture obtained in Reference Example 2-(1), 6.46 g of methanol and 6.46 g (115 mmol) of potassium hydroxide with stirring at room temperature, to which 11.87 g (115 mmol) of butyl nitrite was added dropwise at the same temperature over 2 hours, and the mixture was further stirred at the same temperature for 3 hours. Then, 104 g of the homogeneous solution obtained was divided into two portions.

To 52 g of one of the two-divided solutions was added 50 g of water, followed by extraction and phase separation, and the aqueous layer obtained was washed twice with 25 ml of toluene, cooled to 15° C. and adjusted to pH 1 by use of 36% hydrochloric acid. Then, 50 ml of diethyl ether was added for extraction, followed by phase separation, and the aqueous layer was further extracted twice with 25 ml of diethyl ether. All the ether layers obtained were combined together, and the combined ether layer was washed three times with 30 ml of 10% saline solution, dried with anhydrous sodium sulfate and concentrated, which afforded 13.65 g of a pale pink solid.

The analysis by high performance liquid chromatography revealed that the content of α-hydroxyimino-2-(2,5- dimethylphenoxymethyl)phenylacetonitrile was 95.1%. The yield was 96.5%.

Comparative Example 2

First, 52 g of the other of the two-divided solution in Example 2 was cooled to 15° C. and adjusted to pH 1 by use of 36% hydrochloric acid, to which 50 ml of diethyl ether and 25 ml of water were added, followed by extraction and phase separation. The aqueous layer was further extracted twice with 25 ml of diethyl ether, and all the separated ether layers were combined together, washed three times with 30 ml of 10% saline solution, dried with anhydrous sodium sulfate and concentrated, which afforded 17.65 g of a brown solid.

The content of α-hydroxyimino-2-(2,5-dimethylphenoxymethyl)phenylacetonitrile was 74.5% (the yield was 97.7%).

The content of 1,2-bis(2,5-dimethylphenoxymethyl) benzene was 15%.

Example 3-(1)

To 264.5 g of a toluene solution of a mixture containing 75.40 g (300 mmol) of 2-(2,5-dimethylphenoxymethyl) phenylacetonitrile and 17.54 g (50.6 mmol) of 1,2-bis-(2,5-dimethylphenoxymethyl)benzene, which had been produced in accordance with Reference Example 2-(1) were added 23.57 g (420 mmol) of potassium hydroxide and 58.93 g of n-butanol with stirring at room temperature, to which 142.1 g of a toluene solution containing 37.12 g (360 mmol) of butyl nitrite was added dropwise at the same temperature over 5 hours, and the mixture was further kept at the same temperature for 2.8 hours.

To 486.9 g of the homogeneous solution obtained was added 298 g of water, and the mixture was heated to 50° C. and further kept at the same temperature for 3 hours. This mixture was heated under reduced pressure, and toluene and n-butanol were removed by distillation while adding water to yield 635 g, followed by two washings with 150 g of toluene.

Thus, 624.9 g of an aqueous solution containing 91.15 g (286 mmol, 95.4% yield) of the potassium salt of α-hydroxyimino-2-(2,5-dimethylphenoxymethyl) phenylacetonitrile was obtained, which was neutralized with 36% hydrochloric acid. It was found that 1,2-bis(2,5-dimethylphenoxymethyl)benzene was not found in the aqueous solution, but contained at an amount of 17.43 g (50.3 mmol, 99.4% recovery) in 299 g of the toluene layer after washing.

Example 3-(2)

A mixture comprising 500 g of water, 434 g of toluene, 103.5 g (1.50 mol) of sodium nitrite and 113.4 g (1.53 mol) of n-butanol was cooled to 0° C with stirring, to which 156.3 g (1.50 tool) of 35% hydrochloric acid was added dropwise over 5 hours, and the mixture was further kept at the same temperature for 2 hours. This mixture was subjected to phase separation, and the organic layer was washed twice with 250 g of 4% sodium hydrogencarbonate and further washed with 250 g of 20% saline solution.

The toluene solution of butyl nitrite thus obtained was analyzed by gas chromatography with an internal standard method. As a result, the content of butyl nitrite was 26.1% and the yield was 98.7% on the basis of sodium nitrite.

To 527.2 g of a toluene solution of a mixture containing 155.8 g (0.620 mol) of 2-(2,5-dimethylphenoxymethyl) phenylacetonitrile and 35.1 g (0.101 mol) of 1,2-bis-(2,5-dimethylphenoxymethyl)benzene, which had been obtained in accordance with Reference Example 3-(1), were added 50.3 g (0.896 mol) of potassium hydroxide and 125.7 g of n-butanol with stirring at 22°-25° C., to which 308.3 g of a toluene solution containing 79.2 g (0.768 mol) of butyl nitrite produced in accordance with the foregoing was added dropwise at the same temperature over 5 hours, and the mixture was further kept at the same temperature for 2 hours.

To this reaction mixture was added 620 g of water, and the mixture was heated to 60° C. and further kept at the same temperature for 3 hours. This mixture was heated under reduced pressure, and toluene and n-butanol were removed by distillation while adding water, followed by two washings with 300 g of toluene.

Thus, 1262.7 g of an aqueous solution containing 189.1 g (0.594 mol, 95.8% yield, E/Z =15/85) of the potassium salt of α-hydroxyimino-2-(2,5-dimethylphenoxymethyl) phenylacetonitrile was obtained. It was found that 1,2-bis (2,5-dimethylphenoxymethyl)benzene was not found in the aqueous solution, but contained at an amount of 33.7 g (0.097 mol, 96.1% recovery) in 594 g of toluene after washing.

Reference Example 4

Production of starting material

To 1619 g of toluene were added 788 g (4.5 mol) of α,α'-dichloro-o-xylene, 214 g (1.5 mol) of 4-chloro-2-methylphenol and 24.2 g (0.075 mol) of tetra-n-butylammonium bromide with stirring, to which 1246 g of water was added, and the mixture was heated to 60° C.

To this mixture was added dropwise 244 g (1.65 mol) of 27% aqueous sodium hydroxide solution over 5 hours, and the mixture was kept at the same temperature for 3 hours and then cooled to room temperature. The aqueous layer was removed by phase separation, and the organic layer was washed with 810 g of 5% hydrochloric acid and then washed twice with 810 g of water, after which α,α'-dichloro-o-xylene was removed by distillation to give 381 g of a mixture containing 274 g (0.976 mol, 65.0% yield) of 2-(4-chloro-2-methylphenoxymethyl)benzyl chloride and 82.6 g of (0.213 mol, 28.5% yield) of 1,2-bis(4-chloro-2-methylphenoxymethyl)benzene.

A mixture comprising 196 g of water, 324 g of toluene, 49.0 g (1.0 mol) of sodium cyanide and 12.9 g (0.040 mol) of tetra-n-butylammonium bromide was heated to 80° C. with stirring, to which a mixture of 313 g of toluene and 313 g of the mixture produced in the foregoing was added dropwise over 5 hours, and the mixture was further kept at the same temperature for 3 hours.

Then, the mixture was cooled to room temperature, and the aqueous layer was removed by phase separation, whereas the organic layer was washed three times with 338 g of 5% aqueous sodium hydroxide solution, washed twice with 338 g of water, washed with 338 g of 10% aqueous sodium chloride solution, and then concentrated, which afforded a mixture containing 202 g (0.745 mol, 93.2% yield) of 2-(4-chloro-2-methylphenoxymethyl) phenylacetonitrile and 66.2 g (0.171 mol, 99.4% recovery) of 1,2-bis(4-chloro-2-methylphenoxymethyl)benzene.

Example 4

To 676.1 g of a toluene solution of a mixture containing 188.9 g (695 mmol) of 2-(4-chloro-2-methylphenoxymethyl)phenylacetonitrile and 61.8 g (160 mmol) of 1,2-bis(4-chloro-2-methylphenoxymethyl)benzene, which had been produced in Reference Example 4, were added 56.8 g (978 mmol) of potassium hydroxide and 142 g of n-butanol with stirring at room temperature, to which 86.47 g (839 mmol) of butyl nitrite was added dropwise at the same temperature over 5 hours, and the mixture was further kept at the same temperature for 3 hours.

To 961 g of the homogeneous solution obtained was added 588 g of water, and the mixture was heated under reduced pressure, and toluene and n-butanol were removed by distillation while adding water to yield 1271 g, followed by two washings with 350 g of toluene.

Thus, 1288 g of an aqueous solution containing 239.7 g (707 mmol, 102% yield) of the potassium salt of α-hydroxyimino-2-(4-chloro-2-methylphenoxymethyl) phenylacetonitrile was obtained, which was neutralized with 36% hydrochloric acid. It was found that 1,2-bis(4-chloro-2-methylphenoxymethyl)benzene was not found in the aqueous solution, but contained at an amount of 61.8 g (160 mmol, 100% recovery) in 683 g of the toluene layer after washing.

Industrial Utilizability

According to the process of the present invention, the desired α-hydroxyiminophenylacetonitrile can be produced with high purity, in high yield and with ease by reacting a crude phenylacetonitrile with an alkyl nitrite, extracting the reaction mass with water, and then neutralizing the separated aqueous layer with an acid.

We claim:

1. A process for producing an α-hydroxyiminophenylacetonitrile of the formula [II]:

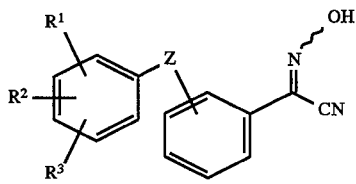

wherein $R^1$, $R^2$ and $R^3$ are the same or different and are independently hydrogen, halogen, nitro, trifluoromethyl, $C_1$-$C_5$ alkyl or $C_1$-$C_5$ alkoxy and Z is —O—, —OCH$_2$—, —S— or —SCH$_2$—, comprising the steps of:

reacting a crude nitrile containing a phenylacetonitrile of the formula [I]:

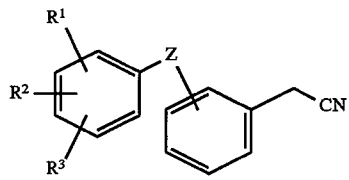

wherein $R^1$, $R^2$, $R^3$ and Z are as defined above, with an alkyl nitrite;

extracting the reaction mixture with water to obtain an aqueous layer; and neutralizing the separated aqueous layer with an acid, wherein the crude nitrile containing the phenylacetonitrile of the formula [I] is produced by reacting a benzyl halide derivative of the formula [IV]:

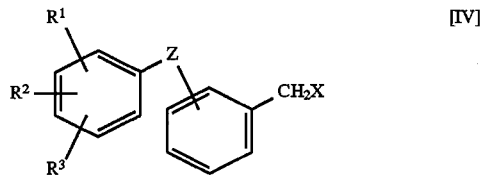

wherein X is halogen, with a cyano compound.

2. A production process according to claim 1, wherein the phenylacetonitrile is selected from the group consisting of 2-phenoxyphenylacetonitrile, 2-(2-methylphenoxymethyl)phenylacetonitrile, 2-(2,5-dimethylphenoxymethyl)phenylacetonitrile and 2-(4-chloro-2-methylphenoxymethyl)phenylacetonitrile.

3. A production process according to claim 1, wherein the alkyl nitrite is selected from the group consisting of methyl nitrite, ethyl nitrite, n-propyl nitrite, isopropyl nitrite, n-butyl nitrite, amyl nitrite and hexyl nitrite.

4. A production process according to claim 1, wherein the Z of the phenylacetonitrile of the general formula [I] is —OCH$_2$— or —SCH$_2$—.

5. A production process according to claim 4, wherein the benzyl halide derivative (IV) is produced by reacting a phenol derivative of the formula [VII]:

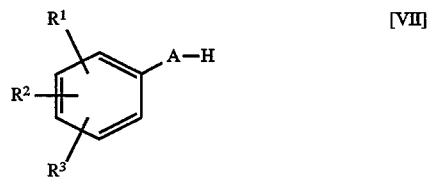

wherein A is —O— or —S— with an α,α'-dihaloxylene derivative of the formula [VI]:

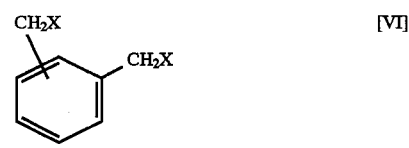

wherein X is halogen.

6. A production process according to claim 1, wherein the benzyl halide derivative [IV] is produced by reacting a toluene derivative of the formula [III]:

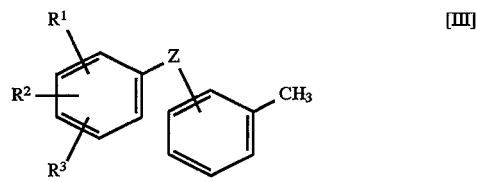

wherein $R^1$, $R^2$, $R^3$ and Z are each as defined in claim 1, with halogen.

7. A process for producing an α-hydroxyiminophenylacetonitrile of the formula [II]:

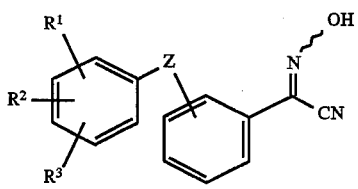

[II]

wherein $R^1$, $R^2$ and $R^3$ are the same or different and are independently hydrogen, halogen, nitro, trifluoromethyl, $C_1$–$C_5$ alkyl or $C_1$–$C_5$ alkoxy and Z is —O—, —OCH$_2$—, —S— or —SCH$_2$—, comprising the steps of:

reacting a crude nitrile containing a phenylacetonitrile of the formula [I]:

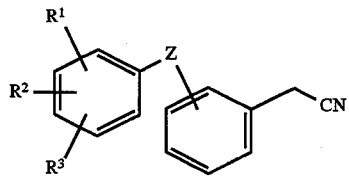

[I]

wherein $R^1$, $R^2$, $R^3$ and Z are as defined above, with an alkyl nitrite in the presence of a base and an organic solvent;

extracting the reaction mixture with water to obtain an aqueous layer containing a base and an organic solvent layer;

separating the aqueous layer from the organic solvent layer; and neutralizing the separated aqueous layer with an acid, wherein the crude nitrile containing the phenylacetonitrile of the formula [I] is produced by reacting a benzyl halide derivative of the formula [IV]:

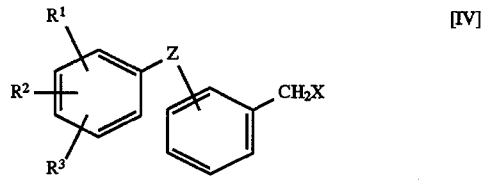

[IV]

wherein X is halogen, with a cyano compound.

8. The method of claim 7, wherein said organic solvent layer contains a hydrophilic organic solvent.

9. The method of claim 7, wherein said organic solvent layer contains a water-insoluble or sparingly water-soluble organic solvent.

* * * * *

UNITED STATES PATENT AND TRADEMARK OFFICE
CERTIFICATE OF CORRECTION

PATENT NO. : 5,629,442
DATED : May 13, 1997
INVENTOR(S) : Takase et al.

It is certified that error appears in the above-indentified patent and that said Letters Patent is hereby corrected as shown below:

In the category "[22] PCT Filed:" change "Jul. 2, 1993" to --Jul. 1, 1994--.

Signed and Sealed this

Sixteenth Day of December, 1997

Attest:

BRUCE LEHMAN

*Attesting Officer*    *Commissioner of Patents and Trademarks*